United States Patent [19]

Nikkels et al.

[11] Patent Number: 5,527,333

[45] Date of Patent: Jun. 18, 1996

[54] SLICING DISPOSABLE BLOOD SAMPLING DEVICE

[75] Inventors: Ben H. Nikkels, Pitman, N.J.; John M. Hegarty, Reading, Mass.; Gregory T. Field, Winthrop, Mass.; Steven Rosone, Burlington, Mass.

[73] Assignee: Graphic Controls Corporation, Buffalo, N.Y.

[21] Appl. No.: 303,811

[22] Filed: Sep. 9, 1994

[51] Int. Cl.⁶ ..................................................... A61B 10/00
[52] U.S. Cl. ............................................................ 606/182
[58] Field of Search ................................ 606/181–183, 606/167; 604/136–137, 157; 128/770

[56] References Cited

U.S. PATENT DOCUMENTS

| | | |
|---|---|---|
| 6,240 | 3/1849 | Ives . |
| 931,791 | 8/1909 | Niergarth . |
| 2,092,812 | 9/1937 | Nemzek . |
| 2,711,738 | 6/1955 | Kelly et al. . |
| 2,823,677 | 2/1958 | Hein, Jr. . |
| 3,010,455 | 11/1961 | Cooper . |
| 3,045,348 | 7/1962 | Dungan . |
| 3,123,212 | 3/1964 | Taylor et al. . |
| 3,192,624 | 7/1965 | Gringer . |
| 3,208,452 | 9/1965 | Stern . |
| 3,299,891 | 1/1967 | Smeton . |
| 3,338,239 | 8/1967 | Mausteller . |
| 3,448,519 | 6/1969 | Tobias . |
| 3,589,357 | 6/1971 | Mabry . |
| 3,659,608 | 5/1972 | Perry . |
| 3,712,293 | 1/1973 | Mielke, Jr. . |
| 3,741,197 | 6/1973 | Sanz et al. . |
| 3,760,809 | 9/1973 | Campbell, Jr. . |
| 3,902,475 | 9/1975 | Begg et al. . |
| 4,064,871 | 12/1977 | Reno . |
| 4,078,552 | 3/1978 | Chen et al. . |
| 4,157,086 | 6/1979 | Maiorano et al. ....................... 128/637 |
| 4,185,634 | 1/1980 | Freedman . |
| 4,360,016 | 11/1982 | Sarrine ..................................... 128/763 |
| 4,416,279 | 11/1983 | Lindner et al. . |
| 4,438,770 | 3/1984 | Unger et al. ............................. 128/637 |
| 4,499,898 | 2/1985 | Knepshield et al. . |
| 4,503,856 | 3/1985 | Cornell et al. . |
| 4,535,769 | 8/1985 | Burns . |
| 4,553,541 | 11/1985 | Burns . |
| 4,628,929 | 12/1986 | Intengan et al. . |
| 4,643,189 | 2/1987 | Mintz . |
| 4,677,979 | 7/1987 | Burns . |
| 4,735,203 | 4/1988 | Ryder et al. . |
| 4,892,097 | 1/1990 | Ranalletta et al. ....................... 606/182 |
| 4,924,879 | 5/1990 | O'Brien ................................... 128/770 |
| 4,949,728 | 8/1990 | Brook ...................................... 128/760 |
| 5,014,718 | 5/1991 | Mitchen ................................... 128/771 |
| 5,026,388 | 6/1991 | Ingalz ...................................... 606/182 |
| 5,133,730 | 7/1992 | Biro et al. ................................ 606/182 |
| 5,314,441 | 5/1994 | Cusack et al. ........................... 606/182 |

OTHER PUBLICATIONS

"The Terderfoot™ Heel Incision Device . . . Pediatrician's Perspective", International Technidyne Corp. brochure, Edison, NJ. May 1992.

Boggs, Robert N., "Redesigned Lancet Reduces Contamination Risk," *Design News,* pp. 100–101 (Apr. 5, 1992).

Burns, Edward R., "Development and Evaluation of a New Instrument for Safe Heelstick Sampling of Neonates," *Laboratory Medicine,* vol. 20, No. 7, pp. 481–481 (Jul. 1989).

*Primary Examiner*—Max Hindenburg
*Attorney, Agent, or Firm*—Ratner & Prestia

[57] ABSTRACT

A disposable blood sampling device for slicing a precise incision of predetermined length and depth in the skin of a patient. The device includes a hollow housing having a top surface with an opening, a front surface, a rear surface, and a bottom surface with an elongated slot adapted to contact the skin of the patient. A trigger is slidably disposed in the opening in the top surface of the housing. A single spring, only, is mounted in the housing in a relaxed, unstressed, and unbiased condition when the device is not actuated. The spring is extended by the trigger when the device is actuated. A cutting blade is coupled to one end of the spring and extends through the elongated slot in the bottom surface of the housing to incise the skin of the patient when the device is actuated. Finally, the device includes a plurality of discrete constraint and restraint elements, positioned in the housing, which collectively form an open guide surface directing the spring, and the blade coupled to the spring, along a predetermined incision path.

40 Claims, 6 Drawing Sheets

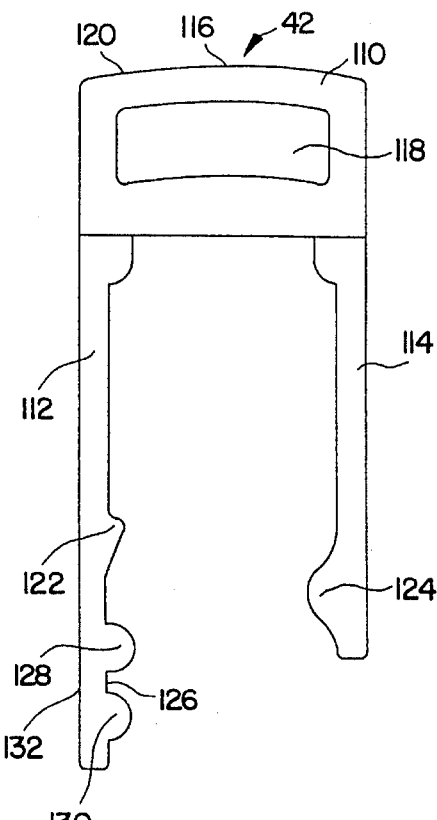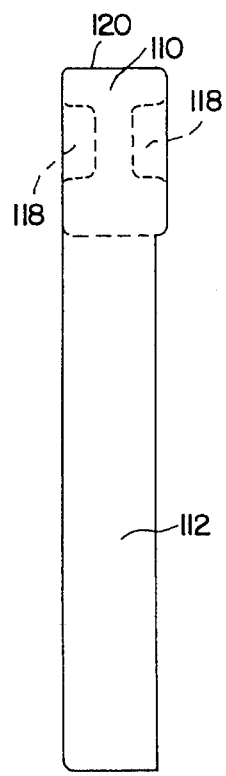
FIG. 5A
FIG. 5B
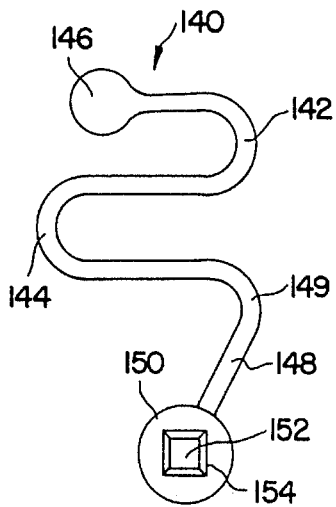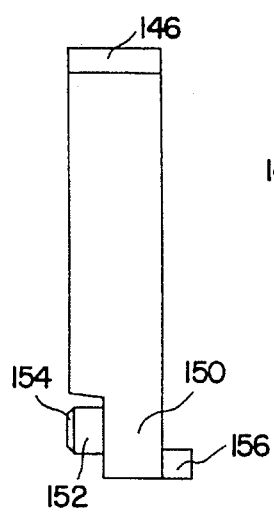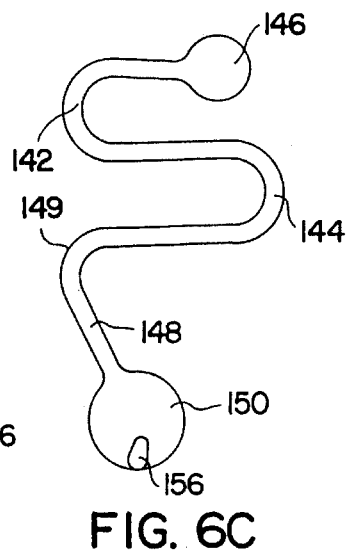
FIG. 6A
FIG. 6B
FIG. 6C
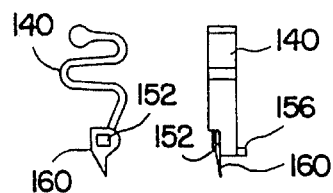
FIG. 7A
FIG. 7B

SLICING DISPOSABLE BLOOD SAMPLING DEVICE

FIELD OF THE INVENTION

This invention relates generally to a device for producing a skin incision in order to cause bleeding and, more specifically, to a disposable blood sampling device capable of producing an incision by slicing rather than puncture without a prestressed or "loaded" spring component.

BACKGROUND OF THE INVENTION

Reproducible incisions are required for a variety of medical procedures. For example, blood samples are drawn routinely from patients (including neonares) for use in numerous types of blood tests such as mandatory screening tests for conditions like phenylketonuria (PKU) and low thyroid function and for measurement of bilirubin levels to monitor jaundice. The blood needed for many tests is conventionally drawn by creating a small incision in the patient's skin. Typically, such incisions are made on the patient's fingertip. For infants or patients with poor circulation, however, the incision can be made in alternate areas such as the foot, arm, or leg.

It is often necessary, as for example when surgery is contemplated or when the patient is a newborn infant, to determine if the patient suffers from a disorder or the effects of medication which may abnormally affect the patient's bleeding time (the time during which blood flows from an incision before coagulation stops the flow). Therefore, in order to test the bleeding time, it is necessary to form a reproducible incision on the patient and to measure the time required for bleeding to stop. The test may be repeated later to check for improvement or deterioration in the bleeding time and, in that case, it is imperative that the incision formed be of approximately the same length and depth as the previous test incision.

The device normally used to create the needed incision in the patient for many medical procedures is a mechanical lancet device. In the development of the art for mechanical lancet devices, many different designs have been created. The most modern of the designs typically are disposable; reusable devices present sterility problems and create a hazard of contamination to both patients and attendants. Such designs also have automatically retractable blades and other operations that prevent their reuse after a single incision has been made and reduce the risk of injury and contamination.

A common feature of the lancet devices is that they make incisions using a plunge cut: the cutting blade is plunged through the skin traveling perpendicular to the skin. One disadvantage of a plunge cut is that the size of the incision matches the size of the cutting blade. Typically, the pointed blade creates a V-shaped incision. The widest region of the incision is on the surface of the skin; the narrowest region of the incision coincides with the deepest point of the incision. Because the narrowest point of the cut is also the deepest point of the cut, a relatively deep incision must be made to ensure that enough capillaries are severed to achieve the necessary bleeding.

Another disadvantage associated with plunge cut lancet devices is that they are painful. A plunge incision is more traumatic than a slice incision. Slice incisions are less intrusive and heal more readily. Moreover, plunge cuts may cause skin tissue, skin fluids, or both to mix with the blood, thereby producing tainted blood samples. Finally, the wide range of skin toughness renders most plunge-type lancet devices unreliable in the accuracy and repeatability of the depth of the cut.

Consequently, slice action devices are often used to create incisions which facilitate blood sampling for medical tests. A blade slices across the patient's skin causing an elongated incision. Conventional slicing lancet devices use a cutting blade that is spring-loaded within a housing. The housing is placed against a patient's skin and the blade is released. The potential energy stored within the spring bias of the blade then causes the blade to exit the housing and to create the needed incision in the patient's skin.

Devices that release the energy stored in a prestressed spring during actuation and to make an incision are often unreliable in the accuracy and repeatability of the incision. Problems exist in accurately and uniformly reproducing, in practice, the tensile strengths and behavior of the spring both in compression and upon release. Such problems are exacerbated when the spring must be incorporated into a relatively inexpensive, disposable product. These difficulties are caused not only by the problems inherent in selecting and properly mounting and pretensioning the spring itself, but also by the problems in maintaining uniformity of the related components with which the spring interacts. Among other problems, dimensions must be accurately maintained and frictional forces must be controlled.

Specifically, for example, a prestressed spring (whether plastic or steel) will creep over time. Creep is accentuated if the device is stored at elevated temperatures; therefore, a shelf-life problem arises. The effect of creep is to change the physical properties of the spring: varying the flight path of the blade and the force to actuate the device, at a minimum, and, in the extreme, risking rupture of the spring.

Some slice action devices use multiple spring arrangements. Such assemblies are relatively complex and require a number of interfitting parts which are relatively difficult to manufacture and accurately assemble. Moreover, the interaction of two oppositely acting springs—typically one to actuate the blade and one to retract the blade—generates a number of design problems.

Finally, a device which incorporates a prestressed spring always risks inadvertent actuation. This is true even if the device incorporates a safety mechanism. The user may remove the safety mechanism well before use of the device is intended.

In many slicing lancet devices, cuts are created which are much longer than they are deep. Consequently, the resulting incision is limited to a body part having a relatively large surface area and is impractical for a fingertip or a neonate. Because sensitive nerve endings populate the skin surface, longer incisions often induce a significant amount of pain in the patient.

In view of the above, it is the principal object of the present invention to provide a simple, automatic device capable of producing and reproducing uniform incisions of precise location, length, and depth to facilitate blood sampling. A related object is to provide a disposable device capable of a single use only. Further objects are to provide a device which is easy to handle and which can be operated with minimal effort.

Another object is to provide a device that creates an incision using a slicing action to provide a clean, sterile cut with reduced trauma to the tissue surrounding the incision and minimal pain to the patient. Furthermore, it is an object to prevent the patient from seeing the often unsettling scene of his or her skin actually being cut and, thereby, to reduce apprehension in a patient.

A further object is to provide such a device which may be readily triggered to form the desired incision but which, before use, may be safely handled and stored without danger of the device being accidentally triggered.

SUMMARY OF THE INVENTION

To achieve these and other objects, and in view of its purposes, the present invention provides a disposable blood sampling device for slicing a precise incision of predetermined length and depth in the skin of a patient. The device includes a hollow housing having a top surface with an opening, a front surface, a rear surface, and a bottom surface with an elongated slot adapted to contact the skin of the patient. A trigger is slidably disposed in the opening in the top surface of the housing. A single spring, only, is mounted in the housing in a relaxed, unstressed, and unbiased condition when the device is not actuated. The spring is extended by the trigger when the device is actuated. A cutting blade is coupled to one end of the spring and extends through the elongated slot in the bottom surface of the housing to incise the skin of the patient when the device is actuated. Finally, the device includes a plurality of discrete constraint and restraint elements, positioned in the housing, which collectively forman open guide surface directing the spring, and the blade coupled to the spring, along a predetermined incision path.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which:

FIG. 5A is a front view of the trigger of the device of FIGS. 1 and 2, shown with the other components of the device removed;

FIG. 5B is a side view of the trigger shown in FIG. 5A;

FIG. 6A is a front view of the spring of the device of FIGS. 1 and 2, shown with the other components of the device removed;

FIG. 6B is a side view of the spring shown in FIG. 6A;

FIG. 6C is a rear view of the spring shown in FIGS. 6A and 6B;

FIG. 7A is a front view of the spring and blade combination of the device of FIGS. 1 and 2, shown with the other components of the device removed;

FIG. 7B is a side view of the spring and blade combination shown in FIG. 7A;

DETAILED DESCRIPTION OF THE INVENTION

Figure 1:
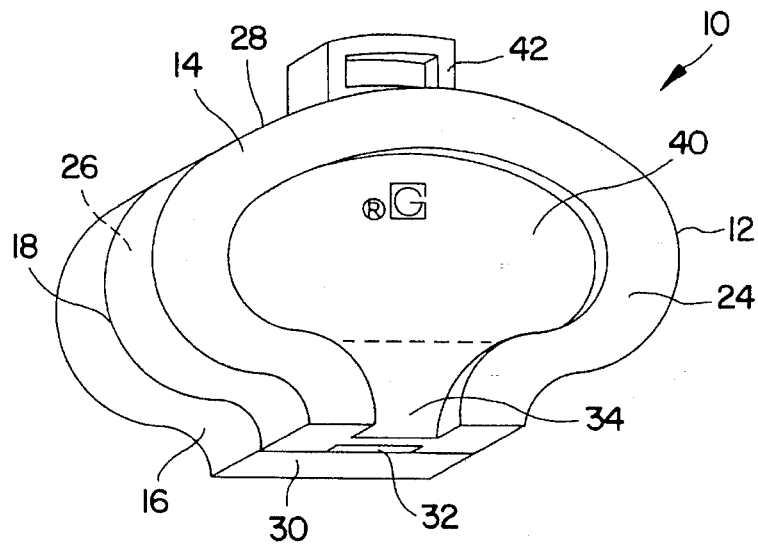
FIG. 1 is a perspective view of a device for the formation of precise incisions in accordance with the present invention.

Referring now to the drawing, wherein like reference numerals refer to like elements throughout, FIG. 1 shows that the retractable, non-reusable blood sampling device 10 of the present invention includes a generally oval shaped housing 12. It is emphasized that, according to common practice, the various elements of the drawing are not to scale. On the contrary, the dimensions of the various elements are arbitrarily expanded or reduced for clarity.

Figure 2:
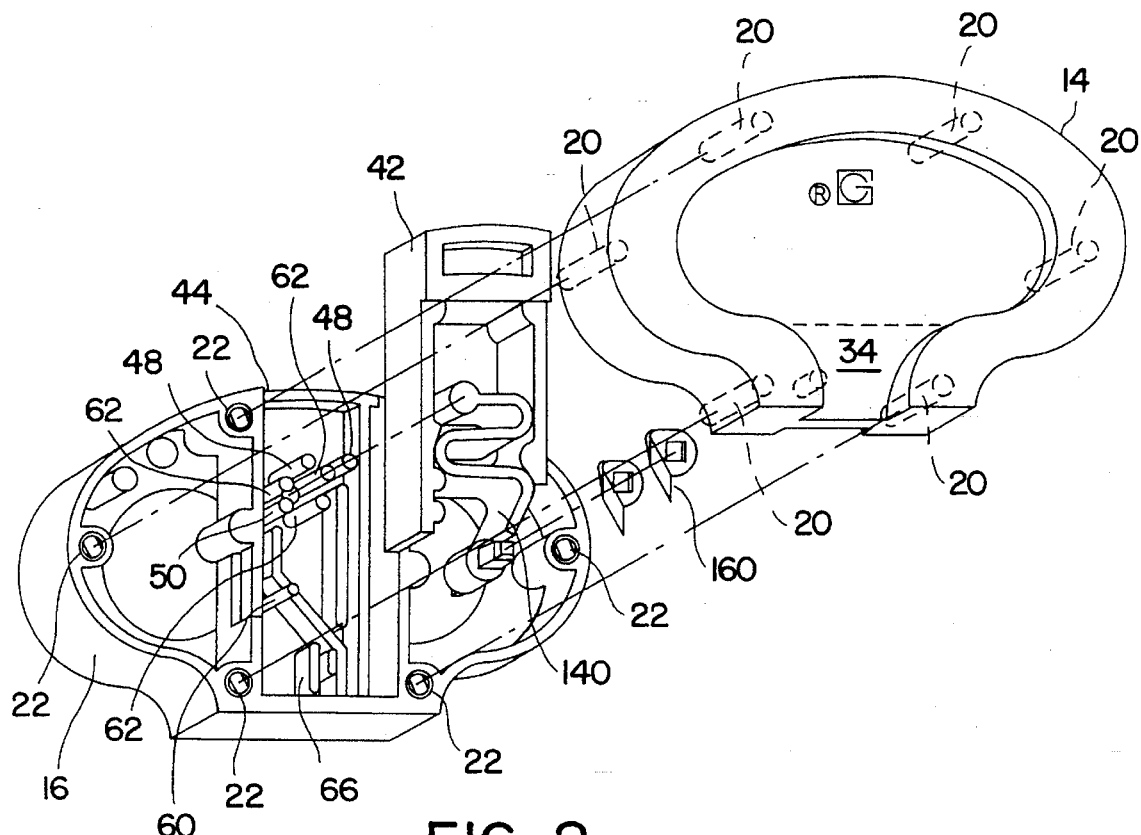
FIG. 2 is an exploded, perspective view of some of the significant components of the device of FIG. 1, illustrated in a disassembled manner.

Housing 12 is preferably formed of two mating halves, a front housing half 14 and a rear housing half 16, which are joined together along a common seam line 18. The housing halves may be joined using any known technique such as glueing, fusing, and the like. A pin and hole construction is illustrated in FIG. 2. Positioned along the circumference of front housing half 14 are dowel pins 20. Dowel pins 20 join with dowel holes 22 in rear housing half 16 when front housing half 14 and rear housing half 16 are pressed together.

Front housing half 14 and rear housing half 16 define a front surface 24 and a rear surface 26, respectively. Housing 12 also has a top surface 28 and a bottom surface 30. Bottom surface 30 has an elongated slot 32. Although slot 32 may be formed in both front housing half 14 and in rear housing half 16 (half of the slot formed in each housing half), as shown in FIG. 1 slot 32 is formed entirely in front housing half 14.

A viewport 34 is provided in front housing half 14 to expose the incision site and, perhaps, previous incision sites to the user. Viewport 34 also serves to indicate to the user the position of slot 32 with respect to the skin of the patient:

viewport 34 coincides in length and position with slot 32. As shown in FIG. 1, viewport 34 may be formed by angling the bottom portion of front housing half 14 toward slot 32. Front housing half 14 may also be made transparent to facilitate the user's view of the incision site.

Figure 3A:
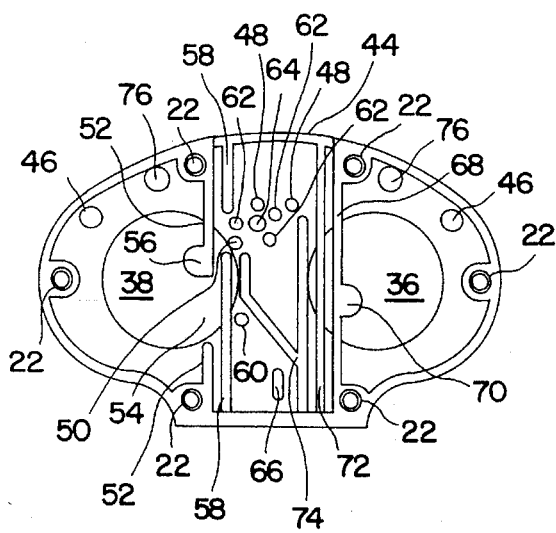
FIG. 3A is a front view of the rear housing half of the device of FIGS. 1 and 2, shown with the other components of the device removed.
Figure 3B:
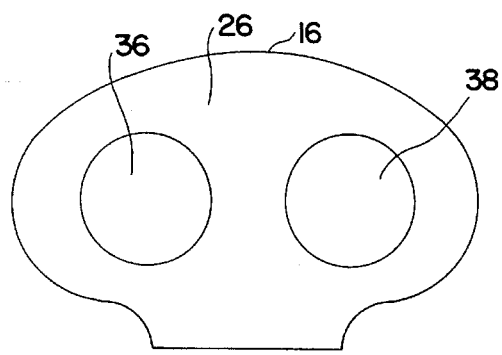
FIG. 3B is a rear view of the rear housing half shown in FIG. 3A.
Figure 3C:
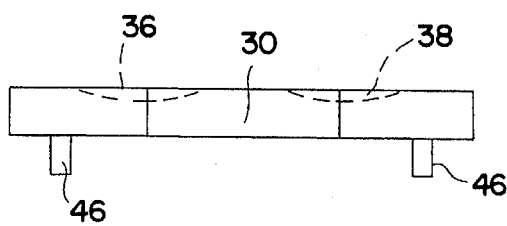
FIG. 3C is a bottom view of the rear housing half shown in FIGS. 3A and 3B.

Although not illustrated in FIG. 1, rear housing half 16 has two, identical finger indentations 36, 38 (see FIGS. 3A, 3B, and 3C). Finger indentations 36, 38 orient device 10 in the user's hand, accommodating both left- and right-handed users, and allow the user to grasp device 10. Front housing half 14 has a thumb indentation 40 to further facilitate grasping and orienting device 10. Indentations 36, 38, 40 allow the user to grasp device 10 even while wearing gloves. Housing 12 is sized and shaped to fit comfortably in the average user's hand. A typical device 10 has a height of about 25 mm, a width of about 9 mm, and a length of about 40 mm. The dimensions can vary, of course, but the unit is relatively small for easy handling with the fingers of one hand.

Also shown in FIG. 1 is the trigger 42. Trigger 42 is the mechanism by which the user of device 10 applies a downward pushing force to actuate device 10. An opening 44 is provided (see FIG. 2) in top surface 28 of housing 12. Opening 44 is formed in both front housing half 14 and in rear housing half 16 (half of opening 44 is formed in each housing half). Trigger 42 extends through, is able to slide within, and fills opening 44.

FIG. 2 is an exploded, perspective view of device 10. As shown, the interior of housing 12 is hollow. Device 10 has five, main components—each of which is discussed in detail below: (1) housing 12, preferably formed by joining front housing half 14 and rear housing half 16; (2) a plastic spring 140 positioned in housing 12 and having a precisely defined, three-dimensional shape; (3) a stainless steel cutting blade 160 coupled to one end of spring 140; (4) a plurality of constraint and restraint elements fixed in housing 12 which direct spring 140 and blade 160 to produce a predetermined incision path of uniform length and depth (which may vary depending upon the size of the patient, e.g., a full-term versus a premature infant); and (5) trigger 42.

FIGS. 3A, 3B, and 3C illustrate rear housing half 16. FIG. 3A is a front view of rear housing half 16 with the other components of device 10 removed. FIGS. 3B and 3C are rear and bottom views, respectively, of rear housing half 16. As discussed above, rear housing half 16 has a series of dowel holes 22 along its circumference. Dowel holes 22 accept dowel pins 20 on front housing half 14 to join the housing halves.

Rear housing half 16 also has a number of first assembly aids 46 which feed plastic during the manufacturing process and orient rear housing half 16 during assembly. First assembly aids 46 nearly contact front housing half 14 (leaving a clearance, assured by second contours 80 on front housing half 14, of about 0.13 mm) when front housing half 14 and rear housing half 16 are joined. First contours 76 of rear housing half 16 assure a similar clearance of about 0.13 mm for second assembly aids 78 on front housing half 14.

First trigger stop posts 48 (two are shown in FIG. 3A) limit the downward travel of trigger 42. First keeper 50 prevents removal of trigger 42 following actuation. A first wall 52 slidably engages trigger 42 to restrict trigger 42 to a vertical travel path. A gap 54 in first wall 52 provides room for trigger 42 to flex as it travels downward. First wall 52 also contains a first ejector pad 56 that helps to push rear housing half 16 out of the mold during the manufacturing process. A first ramp 58 is provided to support the longer leg 112 of trigger 42 (see FIG. 5A) as trigger 42 slides downward relative to housing 12.

The first detent post 60 of rear housing half 16 prevents inadvertent actuation of device 10 (as will be explained below). Gap 54 in first wall 52 allows longer leg 112 of trigger 42 to flex, or bulge, as longer leg 112 passes first detent post 60. First spring anchor posts 62 (three are shown in FIG. 3A) position the anchor lug 146 of spring 140 (see FIG. 9B) on first spring seat 64. A spring restraint 66 engages spring 140 and helps to define the travel path of spring 140 and blade 160. Spring restraint 66 is about 3 mm high and about 1 mm wide.

Like first wall 52, a second wall 68 slidably engages trigger 42 to restrict trigger 42 to a vertical travel path. Second wall 68 also contains a second ejector pad 70 that serves the same function as first ejector pad 56. A second ramp 72 is provided to support the shorter leg 114 (see FIG. 5A) of trigger 42 as trigger 42 slides downward relative to housing 12. Finally, a first spring ramp 74 is provided, having a substantially "Y" shape, to support spring 140 as spring 140 stretches and retracts.

Figure 4A:
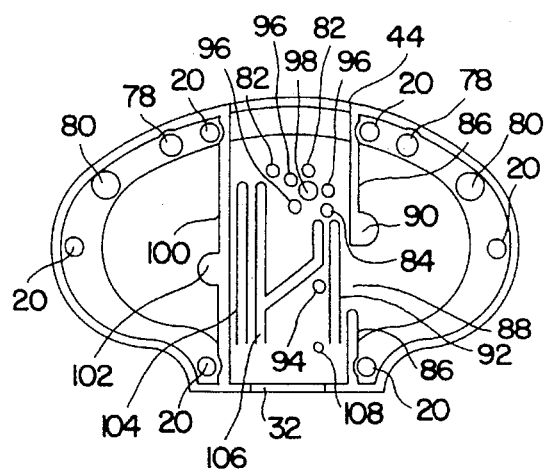
FIG. 4A is a rear view of the front housing half of the device of FIGS. 1 and 2, shown with the other components of the device removed.
Figure 4B:
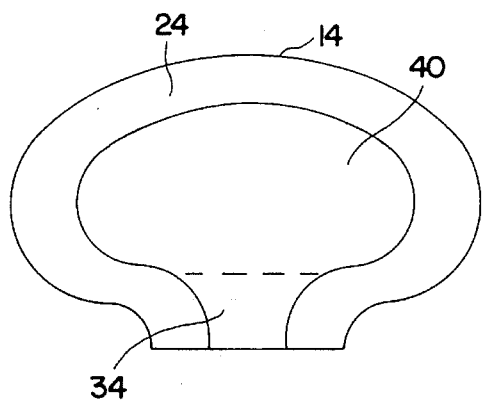
FIG. 4B is a front view of the front housing half shown in FIG. 4A.
Figure 4C:
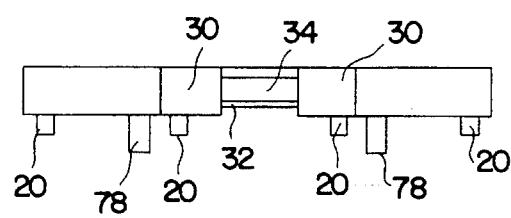
FIG. 4C is a bottom view of the front housing half shown in FIGS. 4A and 4B.

FIGS. 4A, 4B, and 4C illustrate front housing half 14. FIG. 4A is a rear view of front housing half 14 with the other components of device 10 removed. FIGS. 4B and 4C are front and bottom views, respectively, of front housing half 14. As discussed above, front housing half 14 has a series of dowel pins 20 along its circumference. Dowel pins 20 engage dowel holes 22 on rear housing half 16 to join the housing halves.

Front housing half 14 also has a number of second assembly aids 78 which feed plastic during the manufacturing process and orient front housing half 14 during assembly. Second assembly aids 78 nearly contact rear housing half 16 (leaving a clearance, assured by first contours 76 on rear housing half 16, of about 0.13 mm) when front housing half 14 and rear housing half 16 are joined. Second contours 80 of front housing half 14 assure a similar clearance of about 0.13 mm for first assembly aids 46 on rear housing half 16.

Second trigger stop posts 82 (two are shown in FIG. 4A) on front housing half 14 limit the downward travel of trigger 42. Second trigger stop posts 82 mate with first trigger stop posts 48 on rear housing half 16 when housing 12 is assembled. When mated together, second trigger stop posts 82 and first trigger stop posts 48 traverse the entire width of device 10.

Second keeper 84 prevents removal of trigger 42 following actuation. Second keeper 84 mates with first keeper 50 on rear housing half 16 when housing 12 assembled. When mated together, second keeper 84 and first keeper 50 traverse the entire width of device 10.

A third wall 86 slidably engages trigger 42 to restrict trigger 42 to a vertical travel path. A gap 88 in third wall 86 provides room for trigger 42 to flex as it travels downward. Third wall 86 also contains a third ejector pad 90 that helps to push front housing half 14 out of the mold during the manufacturing process. Third wall 86 and gap 88 mate respectively with first wall 52 and gap 54 on rear housing half 16 when housing 12 is assembled. When mated together, first wall 52 and third wall 86, and gaps 54 and 88, each traverse the entire width of device 10. Consequently, first wall 52 and third wall 86 prevent the hollow within an-assembled housing 12 from being compressed by the force of a user's hand when gripping the exterior of housing 12.

A third ramp 92 is provided to support the longer leg 112 of trigger 42 as trigger 42 slides downward relative to housing 12.

The second detent post 94 of front housing half 14 prevents inadvertent actuation of device 10 (as will be explained below). Second detent post 94 mates with first detent post 60 on rear housing half 16 when housing 12 is assembled. When mated together, second detent post 94 and first detent post 60 traverse the entire width of device 10. Gap 88 in third wall 86 allows longer leg 112 of trigger 42 to flex, or bulge, as longer leg 112 passes second detent post 94.

Second spring anchor posts 96 (three are shown in FIG. 4A) position anchor lug 146 of spring 140 (see FIG. 9A) on second spring seat 98. Second spring anchor posts 96 mate with first spring anchor posts 62 on rear housing half 16 when housing 12 is assembled. When mated together, second spring anchor posts 96 and first spring anchor posts 62 traverse the entire width of device 10.

Like third wall 86, a fourth wall 100 slidably engages trigger 42 to restrict trigger 42 to a vertical travel path. Fourth wall 100 also contains a fourth ejector pad 102 that serves the same function as third ejector pad 90. Fourth wall 100 mates with second wall 68 on rear housing half 16 when housing 12 is assembled. When mated together, second wall 68 and fourth wall 100 traverse the entire width of device 10 and, consequently, prevent the hollow within an assembled housing 12 from being compressed by the force of a user's hand when gripping the exterior of housing 12.

A fourth ramp 104 is provided to support the shorter leg 114 of trigger 42 as trigger 42 slides downward relative to housing 12. Finally, a second spring ramp 106 is provided, having a substantially "Y" shape, to support spring 140 as spring 140 stretches and retracts.

Thus, the interior surfaces of front housing half 14 and rear housing half 16 are substantially mirror images of each other. As shown in FIG. 4A, however, front housing half 14 has two components not found in rear housing half 16. First, slot 32 is provided in the front housing half portion of bottom 30. Slot 32 provides an opening through which blade 160 can extend. Second, a stop post 108 is provided on front housing half 14 to help define the travel path of spring 140 and blade 160 and, specifically, to limit the lateral travel of blade 160.

First assembly aids 46, second assembly aids 78, and the full gap formed by gaps 54 and 88 each traverse approximately the full width of device 10—each is just under 9 mm tall. First trigger stop posts 48, first keeper 50, first wall 52, first ejector pad 56, first detent post 60, first spring anchor posts 62, second wall 68, second ejector pad 70, second trigger stop posts 82, second keeper 84, third wall 86, third ejector pad 90, second detent post 94, second spring anchor posts 96, fourth wall 100, fourth ejector pad 102, and stop post 108 each extend about one-half the full width of device 10—each is about 4 mm tall. First ramp 58, spring restraint 66, second ramp 72, and first spring ramp 74 are each about 1 mm tall. First spring seat 64, third ramp 92, second spring seat 98, fourth ramp 104, and second spring ramp 106 are each about 0.5 mm tall.

Turning to FIGS. 5A and 5B, trigger 42 is illustrated in detail. Front view 5A shows that trigger 42 has a rectangular U-shape formed by a head 110, a longer leg 112, and a shorter leg 114. Trigger 42 is rectangular in side view (see FIG. 5B). Longer leg 112 has a height of about 19 mm; shorter leg 114 has a height of about 15 mm. Longer leg 112 and shorter leg 114 each have a length of about 1 mm and a width of about 3 mm. Head 110 of trigger 42 is about 6 mm high at its peak 116, has a length of about 10 mm, has a width of about 4 mm, and may contain a crevice 118.

Crevice 118 helps to reduce "sink" during the manufacturing process in the relatively thick cross-section of head 110 of trigger 42. Sink is the tendency of a portion of plastic which is thick relative to the surrounding plastic to cave, producing an indentation.

The top 120 of head 110 is curved slightly. The curvature of head 110 corresponds with the curvature of top surface 28 of device 10. Thus, when trigger 42 has been actuated and is depressed fully into opening 44, top 120 of trigger 42 is flush with top surface 28 of device 10.

Longer leg 112 has a left actuator 122 which engages spring 140 (as discussed below). Shorter leg 114 has a right actuator 124 which engages spring 140 (also as discussed below). A step 126, defined by a first rib 128 and a second rib 130, is provided on longer leg 112 below left actuator 122.

FIGS. 6A, 6B, and 6C illustrate spring 140. FIG. 6A, a front view of spring 140, shows that spring 140 has a generally "S" shaped configuration defined by a first loop 142 and a second loop 144. An anchor lug 146 is provided on the first end of spring 140, the end which begins first loop 142. Anchor lug 146 fixes the first end of spring 140 between first and second spring anchor posts 62, 96. Anchor lug 146 pivots on first and second spring seats 64, 98.

Anchor lug 146 of spring 140 is precluded from any translation and from rotation in two planes by first and second spring anchor posts 62, 96 and by first and second spring seats 64, 98. Thus, the interaction of anchor lug 146 with first and second spring anchor posts 62, 96 and with first and second spring seats 64, 98 restricts anchor lug 146 to rotation in a single plane, a plane parallel to the length of device 10. Anchor lug 146 is limited to one degree of freedom. Although anchor lug 146 could be fixed on first and second spring seats 64, 98 (as, for example, by glueing, pinning, or the like), reducing anchor lug 146 to zero degrees of freedom, the preferred embodiment leaves anchor lug 146 with one degree of freedom.

First and second spring loops 142, 144 allow spring 140 to flex and provide engagement surfaces for the left and right actuators 122, 124 of trigger 42. The geometry of spring 140 is important because the geometry of spring 140 helps to determine the cutting path of blade 160. In its relaxed position, spring 140 is about 15 mm high. The maximum length of spring 140, defined by an elbow 149 and second spring loop 144, is about 8 mm. The width of spring 140 is about 3 mm. First and second spring loops 142, 144 each have a height of about 3.5 mm.

Second loop 144 of spring 140 extends, via elbow 149, into a tail 148. A blade lug 150 is provided on the second end of spring 140, the end which corresponds to the end of tail 148 opposite second loop 144. Centrally located on one side of blade lug 150 is a blade mounting boss 152. As shown in FIG. 6A, blade mounting boss 152 may be square and may have a forty-five degree chamfer 154 around its end edge. On the side of blade lug 150 opposite blade mounting boss 152, located at the bottom of blade lug 150, is a spring restraint follower 156. Spring restraint follower 156 forces spring 140 to follow a path parallel to the downward movement of trigger 42 (as discussed below).

As shown in FIGS. 7A and 7B, a surgical blade 160 is mounted to blade lug 150 of spring 140. Blade 160 is mounted to blade lug 150 by aligning the aperture 162 in blade 160 (see FIGS. 8A, 8B, and 8C) with blade mounting boss 152 on blade lug 150 and sliding blade 160 onto blade mounting boss 152. (Aperture 162 provides positive orientation and location of blade 160 on spring 140.) Blade 160 is then fixed in position by any known method. For example, ultrasonic energy and pressure can be applied to blade mounting boss 152 to stake blade 160 to blade mounting boss 152. Blade mounting boss 152 becomes molten and flows around and fills aperture 162 in blade 160. When it solidifies, blade mounting boss 152 holds blade 160 firmly in place on blade lug 150. Alternatively, blade 160 may be wedged on blade mounting boss 152.

Figure 8A:
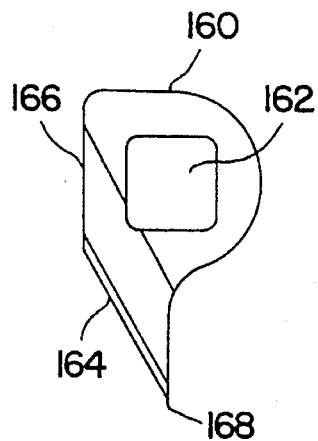
FIG. 8A is a front view of one exemplary blade (suitable for use with a term infant) of the device of FIGS. 1 and 2, shown with the other components of the device removed.

Preferably, blade 160 is made of surgical-grade stainless steel. Device 10 can incorporate a variety of blades 160 of different size depending upon the dimensions of the incision required and upon the size of the patient. FIG. 8A illustrates blade 160 suitable for making an incision in the heel of a full term infant. Blade 160 has a cutting edge 164 and a stop 166. Cutting edge 164 actually makes the incision by slicing the skin. Cutting edge 164 ends in a point 168 which is directed toward slot 32 and helps to determine the depth of the incision. Stop 166 defines, upon contacting stop post 108 on front housing half 14, the end of the lateral cutting path for blade 160.

Figure 8B:
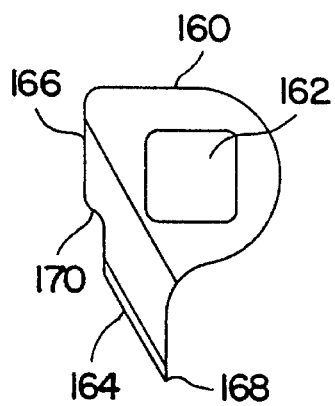
FIG. 8B is a front view of a second exemplary blade (suitable for use with a smaller, premature infant) of the device of FIGS. 1 and 2, shown with the other components of the device removed.

FIG. 8B illustrates blade 160 suitable for making an incision in the heel of an infant born prematurely. Premature infants are typically much smaller than term infants. Accordingly, in addition to cutting edge 164 and stop 166, blade 160 has a shoulder 170 which extends stop 166 so that a smaller incision results.

Figure 8C:
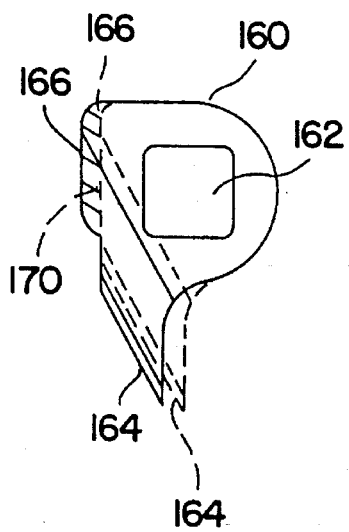
FIG. 8C represents a comparison between the two blades illustrated in FIGS. 8A and 8B.

FIG. 8C represents a comparison between two of the variety of blades 160 which can be used in device 10: a blade suitable for use with term infants and a blade suitable for use with premature infants. The former (illustrated in FIG. 8A) is superimposed over the latter (illustrated in FIG. 8B). FIG. 8C highlights the difference in geometry between stops 166 caused by shoulder 170. This difference and the difference in position of cutting edges 164 help to define the different dimensions for the incisions made by device 10.

The shape of blade 160 is important. As illustrated in FIGS. 8A and 8B, blade 160 can be brought into contact with the skin of the patient with point 168 of blade 160 striking the skin first, exerting maximum pressure to initiate entrance into the skin. Then, as blade 160 travels perpendicularly to the skin, cutting edge 164 exerts maximum shearing force along the direction of the incision to produce a slice rather than a puncture. The preferred angle of cutting edge 164 of blade 160 is about 30 degrees from vertical. By providing a slicing rather than a puncture action to the skin, there is generally less trauma to the skin area around the incision. Consequently, the patient experiences minimal pain and the possibility of a scar after the incision heals is reduced.

All components of device 10, except blade 160, can be fabricated from molded plastic and can be sterilized before use. Housing 12 is easily molded of plastic material, for example, into its two mating halves. Then, after the remaining components are assembled onto rear housing half 16, front housing half 14 is snapped into engagement with rear housing half 16. The economy of materials and assembly permit marketing device 10 as a completely disposable device.

In an alternative embodiment, it is possible to provide device 10 with an integral spring 140 and blade 160. The integral component would be made of steel, rather than plastic, to assure a sharp cutting edge 164. Such a component would avoid the necessity of attaching blade 160 to spring 140.

Figure 9A:
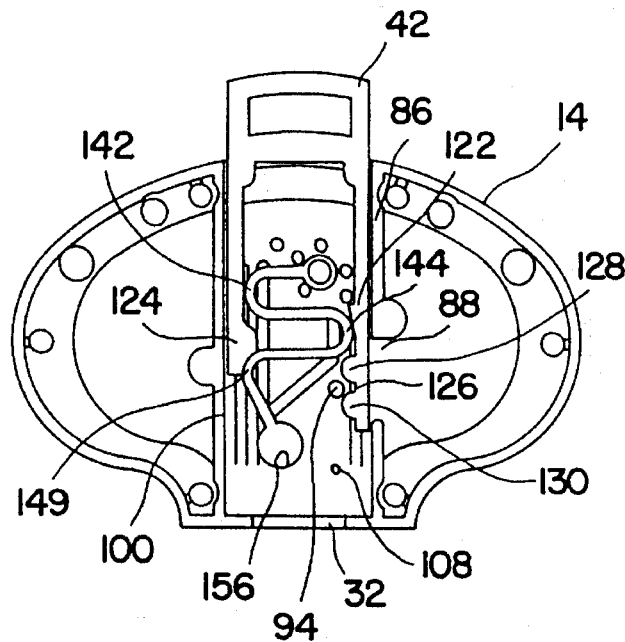
FIG. 9A shows the relationship between the front housing half, the trigger, and the spring of the device of FIGS. 1 and 2 in the "rest" position before (not during) actuation of the device.
Figure 9B:
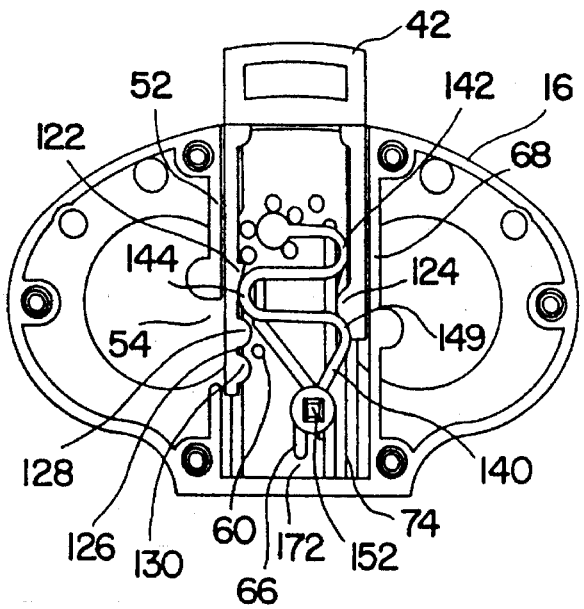
FIG. 9B shows the relationship between the rear housing half, the trigger, and the spring of the device of FIGS. 1 and 2 in the "rest" position before (not during) actuation of the device.

FIG. 9A shows the relationship between front housing half 14, trigger 42, and spring 140 in the "rest" position before (not during) actuation of device 10. Similarly, FIG. 9B shows the relationship between rear housing half 16, trigger 42, and spring 140 in the rest position of device 10.

Device 10 has a only one, single spring 140. The unnecessary complexities of multiple springs are avoided. Even more importantly, spring 140 is maintained in a relaxed condition when device 10 is in the rest position, with a momentarily extended condition during actuation. As shown in FIGS. 9A and 9B, spring 140 is fixed in housing 12 in an unbiased, unstressed, relaxed position before and after actuation. Thus, spring 140 is not pre-loaded, prestressed, or biased when device 10 is not in use.

In the rest position of device 10, head 110 of trigger 42 projects through opening 44 in top surface 28 of device 10. Right actuator 124 of shorter leg 114 rests on elbow 149. Left actuator 122 of longer leg 112 rests on second loop 144 of spring 140 and under first keeper 50 and second keeper 84. Step 126 of longer leg 112 engages first and second detent posts 60, 94. Spring restraint follower 156 is positioned between spring restraint 66 and first spring ramp 74 on rear housing half 16.

Trigger 42 cannot be removed entirely from device 10, even when device 10 is in the rest position before actuation. Thus, the possibility of loss or damage to trigger 42 is avoided. To prevent removal of trigger 42 from opening 44 in top surface 28 of housing 12, an upward force on trigger 42 causes left actuator 122 on longer leg 112 of trigger 42 to abut first and second keepers 50, 84.

The operation of device 10 in accordance with the preferred features of the present invention will now be described. When it is desired to use device 10, the user removes it from its protective package and grasps housing 12 with either the right or left hand. The user places the middle finger in either finger indentation 36 or finger indentation 38, whichever is closer to the palm of the hand. The index finger is allowed to rest against the top 120 of trigger 42 and the thumb engages thumb indentation 40 on front surface 24 of front housing half 14. Thus, device 10 is held between the middle finger and the thumb with the index finger in position to actuate device 10 via trigger 42.

Device 10 is placed against the skin of the patient with slot 32 contacting the skin. The bottom surface 30 of device 10 engages the area of the patient's skin to be incised—typically the heel of a neonate. The user firmly presses device 10 against the skin so that substantially the entire bottom surface 30 of device 10 contacts the skin. Using the index finger, the user presses downward on trigger 42.

To prevent accidental triggering and, therefore, inadvertent actuation, a safety mechanism is provided. Step 126 on trigger 42 cooperates with first and second detent posts 60, 94 and with gaps 54 and 88 to provide a safety against accidental triggering. Step 126 provides resistance against downward movement of trigger 42. Before actuation, step 126 brackets first and second detent posts 60, 94 with first rib 128 resting on top of first and second detent posts 60, 94 and second rib 130 lying underneath first and second detent posts 60, 94. As the user presses downward on trigger 42 to actuate device 10, first rib 128 is forced against first and second detent posts 60, 94 and trigger 42 (and, consequently, the user) meets resistance.

Further downward force causes the portion 132 of longer leg 112 opposite step 126 to flex or bulge into the area defined by gaps 54 and 88. This allows first rib 128 to slide around first and second detent posts 60, 94 and permits trigger 42 to continue downward travel. Once the force necessary to overcome the resistance caused by the interaction between step 126 and first and second detent posts 60, 94 is sufficient, the inertia of the user's downwardly moving finger on trigger 42 ensures that the full downward movement of trigger 42 occurs.

The geometry of step 126 (including first and second ribs 128, 130) and first and second detent posts 60, 94, together with the flexibility of leg portion 132 of trigger 42, define initial resistance which must be overcome to actuate device 10. These factors can be designed to achieve a wide variety of desired initial (or "break-away") resistances. A trade-off exists between a sufficiently large initial resistance to assure safety and a sufficiently small initial resistance to permit ease of operation. An initial resistance overcome by a force of about 0.5 to 1.75 pounds (8 to 28 ounces) is suitable.

Once the initial resistance is overcome, there follows a rapid acceleration of the trigger downward. The inertia developed by the user's finger on trigger 42, in overcoming the initial resistance, is used to depress trigger 42 completely. If the user could stop the downward force of his or her finger on trigger 42 after step 126 clears first and second detent posts 60, 94, then spring 140 (because spring 140 is not prestressed) would not move. The user must continue to push downward on trigger 42 to apply force to blade 160 through spring 140. The user does so without thinking, through inertia.

Figure 10:
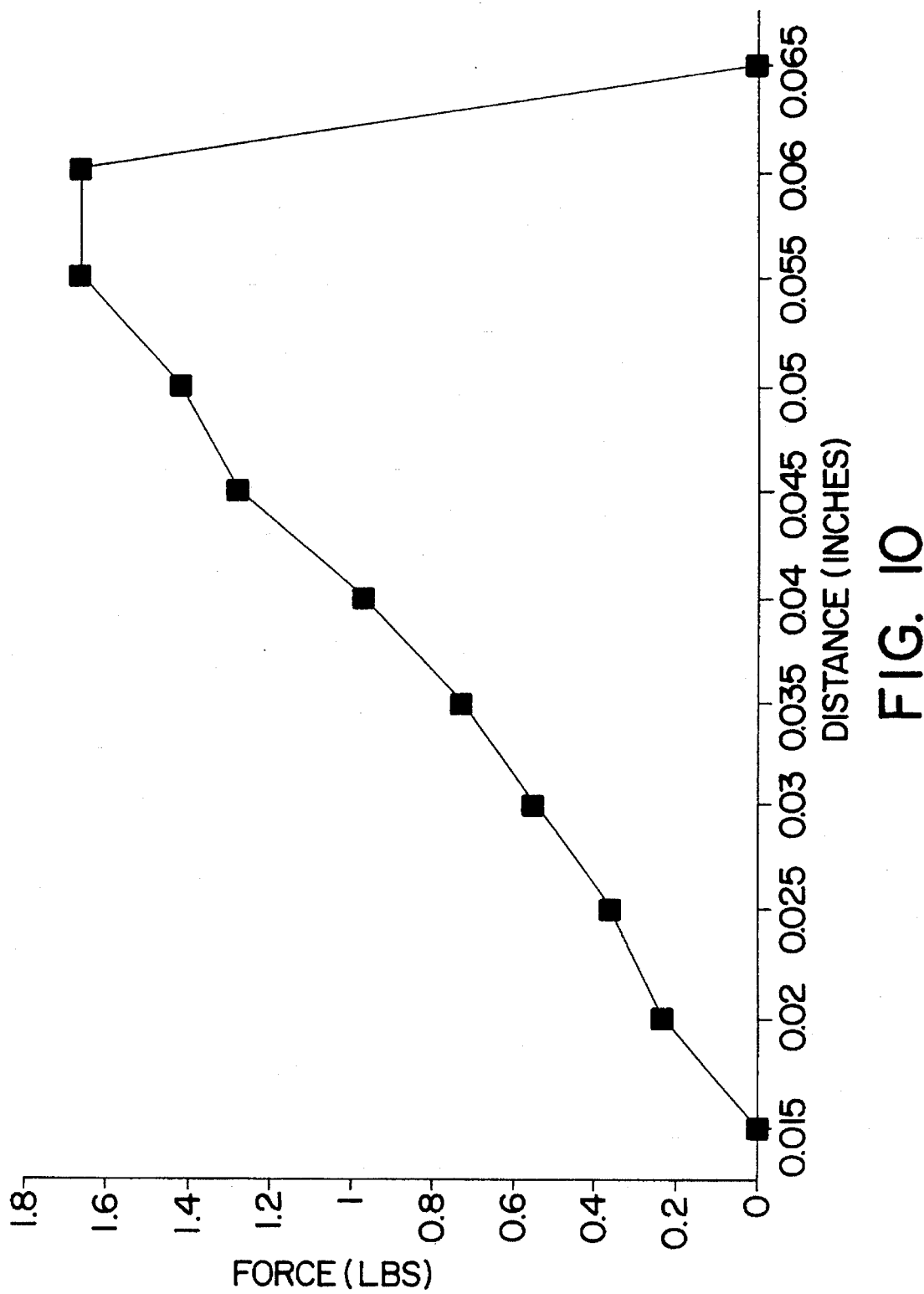
FIG. 10 presents a graph of the force (in pounds) applied by the user to the trigger versus the depression distance (in inches) of the trigger under that force.

FIG. 10 presents a graph of the force (in pounds) applied by the user to trigger 42 versus the depression distance (in inches) of trigger 42—and, consequently, in large measure of spring 140—under that force. Depression of trigger 42 gradually increases under increasing force until the applied force reaches an actuation value. During this period, first rib 128 begins to slide around first and second detent posts 60, 94 and trigger 42 begins to travel downward. Once first rib 128 clears first and second detent posts 60, 94 (under the actuation force), the initial resistance is overcome and trigger 42 accelerates rapidly downward under the decreasing force of inertia until trigger 42 is fully depressed.

As shown in FIG. 10, the actuation force for the prototype tested was about 1.7 pounds (or 27 ounces). An actuation force of between about 0.5 to 1.75 pounds (8 to 28 ounces) is suitable; an actuation force of about 1 pound (16 ounces) is preferable.

Trigger 42 is constrained to move vertically downward, toward bottom surface 30 of housing 12, by first wall 52, second wall 68, third wall 86, and fourth wall 100. As trigger 42 is depressed, right actuator 124 on shorter leg 114 of trigger 42 pushes downward on elbow 149 of spring 140. Simultaneously, left actuator 122 of longer leg 112 of trigger 42 pushes downward on second loop 144 of spring 140. The downward forces on elbow 149 and second loop 144 of spring 140 stretch spring 140 downward.

As spring 140 stretches downward, spring restraint follower 156 slides downward between spring restraint 66 and first spring ramp 74. Thus, spring restraint follower 156 constrains spring 140 to follow a vertical path parallel to the downward movement of trigger 42. Spring 140 also stores potential energy as it stretches.

Spring 140 is stretched, by the downward inertial force of trigger 42, to a point where spring restraint follower 156 reaches the channel 172 between the bottom of spring restraint 66 and bottom surface 30 of housing 12. At this point, blade 160 extends out of slot 32 and into the patient's skin. Also at precisely this point, left actuator 122 of trigger 42 will have just pushed past second loop 144 of spring 140. Right actuator 124 of trigger 42 will still contact elbow 149 of spring 140, thereby creating a downward, diagonal force on spring 140. Once right actuator 124 of trigger 42 is pushed past elbow 149 of spring 140, there is no longer any downward force on spring 140. When spring restraint follower 156 reaches channel 172, therefore, the potential energy stored in spring 140 causes spring restraint follower 156 to move laterally through channel 172. Blade lug 150 and blade 160 follow spring restraint follower 156 and also move laterally.

A part of the potential energy, stored in stretched spring 140, is released to force blade 160 to cut laterally. Trigger 42 does not release energy stored in spring 140; rather, trigger 42 stretches or extends spring 140 creating potential energy released when spring 140 reaches the end of spring restraint 66. The lateral movement of blade 160 concludes when stop 166 on blade 160 contacts stop post 108 on first housing half 14. Subsequently, spring 140 and blade 160 move upward under the restoring force of spring 140. Spring 140 will retract until it attains its initial, rest position.

Thus, blade 160 is automatically retracted (withdrawn into housing 12) immediately after the incision has been made. Resilient spring 140 forces blade 160 upward, causing blade 160 to be removed from the patient's skin and withdrawn into housing 12. In this position, blade 160 is safely held inside housing 12 out of potential contact with anyone, including the patient and attendants, thereby reducing the potential for laceration or infection. Moreover, no special handling precautions need be used for safe disposal of device 10. Device 10 should be properly discarded just after an incision has been made.

Blade 160 traverses slot 32 in an extremely short period of time (milliseconds). The tremendous speed of device 10—combined with a precise, non-tearing, sliced incision and a controlled depth of cut—reduces the sensation of pain. It is believed that blade 160 is retracted from the skin before nerve impulses can reach the brain. In addition to its speed, device 10 is essentially noiseless; if the patient is stressed, the blood oxygen level may decrease and render certain blood tests inaccurate.

Once device 10 is triggered and blade 160 cuts and retracts, trigger 42 locks flush with top surface 28 of housing 12. The locking action of trigger 42 and the retraction of blade 160 prevent the reuse of device 10 and reduce the risk of accidental injury. Following actuation, trigger 42 is completely depressed: top 120 of trigger 42 is flush with top surface 28 of housing 12; the underside of head 110 of trigger 42 contacts first and second trigger stop posts 48, 82; and longer leg 112 of trigger 42 contacts bottom surface 30 of housing 12. Left actuator 122 is positioned under second loop 144 of spring 140 and right actuator 124 is positioned under elbow 149.

Nothing is available for the user to grasp trigger 42 and re-set device 10 because trigger 42 is held completely within housing 12. Even if the user were able to grasp and pull upward on trigger 42, the user would be unable to remove trigger 42 from housing 12. An upward force on trigger 42 following actuation will cause left actuator 122 to push upward on second loop 144 of spring 140 (and, simultaneously, right actuator 124 to push upward on elbow 149). Second loop 144 will contact first and second keepers 50, 84—preventing any further upward movement of spring 140 or trigger 42. Trigger 42 is locked in housing 12, a condition which prevents reactivation of device 10.

The user, by depressing trigger 42, controls the actuation of device 10. Once actuated, however, device 10 is completely automatic. The user applies only a vertical force to trigger 42 of device 10. Spring 140 is guided along its travel path by a number of discrete elements which transfer that vertical force into an incision. Such elements collectively constitute an open, rather than a closed, guide surface. Throughout its travel path, spring 140 slides along first spring ramp 74 and second spring ramp 106.

It is desirable to create a perfectly linear incision in a patient to minimize tissue damage surrounding the incision. Accordingly, side-to-side travel or wobbling of blade 160 during operation must be minimal. A wobbling blade causes inconsistencies along the edges of the incision which affect the surrounding tissue and make it harder for the tissue to heal. Ramps 58, 72, 74, 92, 104, and 106 help to assure that spring 140 and, hence, blade 160, travel a substantially linear path.

Figure 11A:
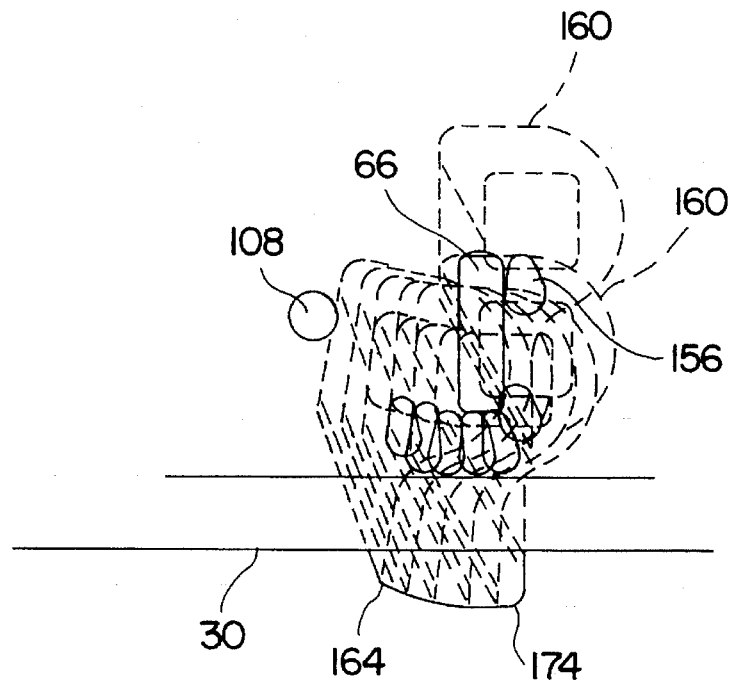
FIG. 11A depicts the trajectory of the blade (suitable for use with a term infant) shown in FIG. 8A.
Figure 11B:
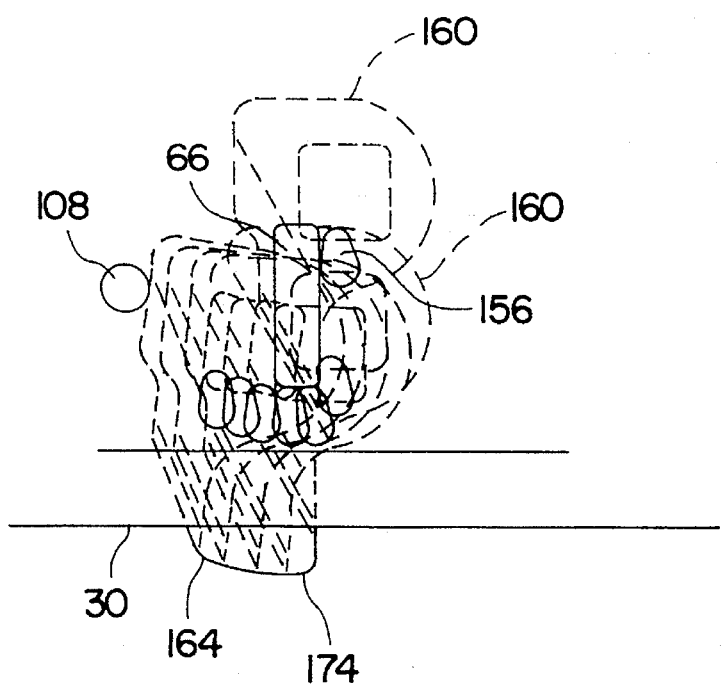
FIG. 11B depicts the trajectory of the blade (suitable for use with a premature infant) shown in FIG. 8B.

An incision makes a cleaner cut than a stab or puncture, resulting in better blood flow with less chance of trauma or scarring. Accordingly, cutting edge 164 enters the skin at an angle. This creates a slicing action. In FIGS. 11A and 11B, the shape of the incision path 174 made by blade 160 into the tissue of a patient is shown. FIG. 11A depicts the trajectory of blade 160 (suitable for use with a term infant) shown in FIG. 8A; FIG. 11B depicts the shallower trajectory of blade 160 (suitable for use with a premature infant) shown in FIG. 8B. The position of blade 160 at various points along incision path 174, during the operation of device 10, is illustrated in each figure.

Incision path 174 is substantially trapezoidal in shape. Blade 160 does not plunge into the tissue of a patient. Rather, as blade 160 follows its initial trajectory, there is both a horizontal and a vertical component to the movement of cutting edge 164. Consequently, blade 160 slices the tissue of the patient, cutting across the tissue of the patient as blade 160 descends into, traverses, and ascends from the tissue of the patient. Blade 160 makes a narrow slice into the patient's tissue without the adverse effects of plunging a blade into tissue.

Incision path 174 shown in FIG. 11A makes an incision about 1 mm deep and 2.5 mm long. Incision path 174 shown in FIG. 11B makes an incision about 0.8 mm deep and 1.8 mm long. A narrow, relatively shallow slice provides the desired capillary, not venal, blood and decreases the possibility of stress in the patient. A narrow slice having a predetermined length and depth assures sufficient blood flow for testing.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A disposable device for slicing a precise incision of predetermined length and depth in the skin of a patient comprising:

a hollow housing having a top surface with an opening, a front surface, a rear surface, and a bottom surface with an elongated slot adapted to contact the skin of the patient;

a trigger slidably disposed in said opening in said top surface of said housing;

a single spring for said device mounted in said housing in a relaxed, unstressed, and unbiased condition when said device is not actuated and extended by said trigger when said device is actuated, said spring having a first end and a second end;

a cutting blade coupled to said second end of said spring and extending through said elongated slot in said bottom surface of said housing to slice the skin of the patient when said device is actuated; and a plurality of discrete constraint and restraint elements positioned in said housing forming an open guide surface directing said spring, and said blade coupled to said spring, to slice rather than puncture along a predetermined incision path.

2. A device according to claim 1 wherein said housing has a viewport permitting observation of the skin of the patient where the incision will be made.

3. A device according to claim 2 wherein said viewport is an inwardly slanted section of said front surface of said housing, slanting downward toward said elongated slot in said bottom surface of said housing and corresponding in length with said elongated slot.

4. A device according to claim 1 wherein at least a portion of said housing is transparent.

5. A device according to claim 1 wherein said rear surface of said housing has at least one finger indentation and said front surface of said housing has a thumb indentation, said at least one finger indentation and said thumb indentation facilitating handling of said device.

6. A device according to claim 1 wherein said spring has an anchor lug integrally formed on said first end of said spring, said anchor lug mounting said spring in said housing.

7. A device according to claim 6 wherein said housing has a plurality of spring anchor posts limiting said anchor lug of said spring to a single degree of freedom and fixing said anchor lug rotatably in said housing.

8. A device according to claim 1 wherein said spring has a blade lug integrally formed on said second end of said spring, said blade lug having a blade mounting boss onto which said blade is mounted.

9. A device according to claim 1 wherein said spring is resilient plastic.

10. A device according to claim 1 wherein said housing has a spring ramp supporting said spring and upon which said spring slides as said spring extends and retracts.

11. A device according to claim 1 wherein said blade has a cutting edge with a point directed toward said elongated slot in said bottom surface of said housing, said cutting edge angled about thirty degrees from vertical.

12. A device according to claim 11 wherein said blade is surgical grade stainless steel.

13. A device according to claim 1 wherein said spring and said blade are integral and surgical grade stainless steel.

14. A device according to claim 1 wherein said plurality of discrete constraint and restraint elements include:

(a) a stop post positioned in said hollow housing, (b) a stop positioned on said blade and contacting said stop post to limit horizontal motion of said blade, (c) a spring restraint positioned in said hollow housing forming a channel between said spring restraint and said bottom surface of said housing, said spring restraint directing the vertical motion of said blade and said channel directing the horizontal motion of said blade, and (d) a spring restraint follower located on said second end of said spring and opposite said blade and traversing along said spring restraint and through said channel.

15. A device according to claim 14 wherein said blade has a shoulder extending said stop and further limiting horizontal motion of said blade.

16. A device according to claim 1 further comprising means for limiting the sliding of said trigger.

17. A device according to claim 16 wherein said limiting means includes at least one trigger stop post positioned in said hollow housing, said trigger contacting said at least one trigger stop post and lying flush with said top surface of said housing when said trigger is fully depressed in said opening in said top surface of said housing and said device is fully actuated.

18. A device according to claim 1 further comprising means for preventing removal of said trigger from said opening in said top surface of said housing after actuation of said device.

19. A device according to claim 18 wherein said preventing means includes a keeper positioned in said hollow housing.

20. A device according to claim 1 further comprising means for restricting said trigger to a vertical travel path through said opening in said top surface of said housing.

21. A device according to claim 20 wherein said restricting means includes a pair of walls positioned in said hollow housing.

22. A device according to claim 1 wherein said housing has a plurality of ramps supporting said trigger and upon which said trigger slides.

23. A device according to claim 1 further comprising means for precluding inadvertent actuation of said device.

24. A device according to claim 23 wherein said precluding means includes:

(a) a detent post positioned in said hollow housing, and (b) a flexible leg on said trigger having a first rib resting on top of said detent post before actuation of said device and precluding downward motion of said trigger until a predetermined actuation force is applied to said trigger and said first rib slides around said detent post thereby actuating said device.

25. A device according to claim 1 wherein said spring is a substantially "S" shape having a first loop extending from said first end, an oppositely directed second loop extending from said first loop, a tail extending from said second loop and terminating in said second end, and an elbow disposed between said second loop and said tail.

26. A device according to claim 25 wherein said trigger is a substantially "U" shape having a head upon which actuation force is applied, a longer leg with a left actuator engaging said second loop of said spring and transferring actuation force from said trigger to said spring, and a shorter leg having a right actuator engaging said elbow of said spring and transferring actuation force from said trigger to said spring.

27. A device according to claim 1 further comprising means for automatically retracting said blade into said housing after actuation of said device.

28. A device according to claim 1 further comprising means for prohibiting removal of said trigger from said opening in said top surface of said housing before actuation of said device.

29. A device according to claim 28 wherein said prohibiting means includes:

(a) a detent post positioned in said hollow housing, (b) a keeper positioned in said hollow housing, and (c) a flexible leg on said trigger having a second rib lying underneath said detent post and a left actuator lying underneath said keeper, said second rib abutting said detent post and said left actuator abutting said keeper when said trigger is pulled upward.

30. A disposable device for slicing a precise incision of predetermined length and depth in the skin of a patient comprising:

a hollow housing having a top surface with an opening, a front surface, a rear surface, a bottom surface with an elongated slot adapted to contact the skin of the patient, and a plurality of spring anchor posts;

a single, substantially "S"-shaped spring mounted in said housing in a relaxed, unstressed, and unbiased condition when said device is not actuated, said spring having (a) a first end, (b) an anchor lug integrally formed on said first end of said spring, said anchor lug fixed by said spring anchor posts of said housing and mounting said spring in said housing, (c) a second end, (d) a first loop extending from said first end, (e) an oppositely directed second loop extending from said first loop, (f) a tail extending from said second loop and terminating in said second end, and an elbow disposed between said second loop and said tail;

a substantially "U"-shaped trigger slidably disposed in said opening in said top surface of said housing and having a head upon which actuation force is applied, a longer leg with a left actuator engaging said second loop of said spring and transferring actuation force from said trigger to extend said spring, and a shorter leg having a right actuator engaging said elbow of said spring and transferring actuation force from said trigger to extend said spring;

a cutting blade coupled to said second end of said spring and extending through said elongated slot in said bottom surface of said housing to incise the skin of the patient when said device is actuated; and a plurality of discrete constraint and restraint elements positioned in said housing forming an open guide surface directing said spring, and said blade coupled to said spring, along a predetermined incision path.

31. A device according to claim 30 wherein said housing has a viewport permitting observation of the skin of the patient where the incision will be made.

32. A device according to claim 30 wherein said rear surface of said housing has at least one finger indentation and said front surface of said housing has a thumb indentation, said at least one finger indentation and said thumb indentation facilitating handling of said device.

33. A device according to claim 30 wherein said spring is resilient plastic.

34. A device according to claim 30 wherein said plurality of discrete constraint and restraint elements include:

(a) a stop post positioned in said hollow housing, (b) a stop positioned on said blade and contacting said stop post to limit horizontal motion of said blade, (c) a spring restraint positioned in said hollow housing forming a channel between said spring restraint and said bottom surface of said housing, said spring restraint directing the vertical motion of said blade and said channel directing the horizontal motion of said blade, and (d) a spring restraint follower located on said second end of said spring and opposite said blade and traversing along said spring restraint and through said channel.

35. A device according to claim 30 wherein said hollow housing has at least one trigger stop post, said trigger contacting said at least one trigger stop post and lying flush with said top surface of said housing when said trigger is fully depressed in said opening in said top surface of said housing and said device is fully actuated.

36. A device according to claim 30 wherein said hollow housing has a keeper preventing removal of said trigger from said opening in said top surface of said housing after actuation of said device.

37. A device according to claim 30 wherein said hollow housing has a pair of walls restricting said trigger to a vertical travel path through said opening in said top surface of said housing.

38. A device according to claim 30 wherein said hollow housing has a detent post and said trigger has a flexible leg with a first rib, said first rib resting on top of said detent post before actuation of said device and precluding downward motion of said trigger until a predetermined actuation force is applied to said trigger and said first rib slides around said detent post thereby actuating said device.

39. A device according to claim 30 wherein said hollow housing has a detent post and a keeper and said trigger has a flexible leg with a second rib lying underneath said detent post and a left actuator lying underneath said keeper, said second rib abutting said detent post and said left actuator abutting said keeper when said trigger is pulled upward.

40. A disposable device for slicing a precise incision of predetermined length and depth in the skin of a patient comprising:

- a hollow housing having a top surface with an opening, a front surface having a thumb indentation facilitating handling of said device, a rear surface having at least one finger indentation facilitating handling of said device, a bottom surface with an elongated slot adapted to contact the skin of the patient, and a viewport permitting observation of the skin of the patient where the incision will be made;
- a trigger slidably disposed in said opening in said top surface of said housing and having a flexible leg with a left actuator, a first rib, and a second rib;
- a single, resilient, plastic spring mounted in said housing in a relaxed, unstressed, and unbiased condition when said device is not actuated and extended by said trigger when said device is actuated, said spring having a first end and a second end;
- a cutting blade coupled to said second end of said spring and extending through said elongated slot in said bottom surface of said housing to incise the skin of the patient when said device is actuated;
- a stop post positioned in said hollow housing;
- a stop positioned on said blade and contacting said stop post to limit horizontal motion of said blade;
- a spring restraint positioned in said hollow housing forming a channel between said spring restraint and said bottom surface of said housing, said spring restraint directing the vertical motion of said blade and said channel directing the horizontal motion of said blade;
- a spring restraint follower located on said second end of said spring and opposite said blade and traversing along said spring restraint and through said channel;
- at least one trigger stop post positioned in said hollow housing, said trigger contacting said at least one trigger stop post and lying flush with said top surface of said housing when said trigger is fully depressed in said opening in said top surface of said housing and said device is fully actuated;
- a keeper positioned in said hollow housing preventing removal of said trigger from said opening in said top surface of said housing after actuation of said device;
- a pair of walls positioned in said hollow housing restricting said trigger to a vertical travel path through said opening in said top surface of said housing;
- a detent post positioned in said hollow housing, said first rib of said flexible leg of said trigger resting on top of said detent post before actuation of said device and precluding downward motion of said trigger until a predetermined actuation force is applied to said trigger and said first rib slides around said detent post thereby actuating said device, said second rib of said flexible leg of said trigger lying underneath said detent post and said left actuator of said flexible leg of said trigger lying underneath said keeper with said second rib abutting said detent post and said left actuator abutting said keeper when said trigger is pulled upward.

* * * * *